(12) United States Patent
Mahlmann

(10) Patent No.: US 7,335,023 B2
(45) Date of Patent: Feb. 26, 2008

(54) ASPIRATOR HAVING A CUSHIONED AND ASPIRATION CONTROLLING TIP

(76) Inventor: Lee A. Mahlmann, 4411 Avenue N., Rosenberg, TX (US) 77471

( * ) Notice: Subject to any disclaimer, the term of this patent is extended or adjusted under 35 U.S.C. 154(b) by 0 days.

(21) Appl. No.: 11/414,989

(22) Filed: May 1, 2006

(65) Prior Publication Data
US 2006/0199147 A1 Sep. 7, 2006

Related U.S. Application Data

(63) Continuation-in-part of application No. 11/323,876, filed on Dec. 31, 2005, now abandoned, and a continuation-in-part of application No. 10/909,725, filed on Aug. 2, 2004, now abandoned.

(60) Provisional application No. 60/514,477, filed on Oct. 27, 2003.

(51) Int. Cl.
*A61C 17/06* (2006.01)

(52) U.S. Cl. .......................... 433/96; 433/91; 433/136; 604/268

(58) Field of Classification Search .................. 433/91, 433/92, 94, 95, 96, 93; 604/128, 131, 268; 15/300.1
See application file for complete search history.

(56) References Cited

U.S. PATENT DOCUMENTS

| | | | | |
|---|---|---|---|---|
| 3,091,859 A * | 6/1963 | Baughan | ...................... | 433/94 |
| 3,541,583 A * | 11/1970 | Deuschle | ..................... | 433/96 |
| 3,590,820 A * | 7/1971 | Nehra et al. | ................. | 604/268 |
| 3,881,254 A * | 5/1975 | Epstein | ......................... | 433/96 |
| 3,913,231 A * | 10/1975 | Orsing | ......................... | 433/96 |
| 3,913,577 A * | 10/1975 | Nehra et al. | ................. | 604/268 |
| 3,965,901 A * | 6/1976 | Penny et al. | ................. | 604/119 |
| 4,221,220 A * | 9/1980 | Hansen | ........................ | 604/119 |
| 5,114,342 A * | 5/1992 | Young et al. | .................. | 433/95 |
| 5,728,078 A * | 3/1998 | Powers, Jr. | .................. | 604/246 |
| 5,743,736 A * | 4/1998 | Folko et al. | ................... | 433/96 |
| 6,068,477 A * | 5/2000 | Mahlmann | .................... | 433/96 |
| 6,183,254 B1 * | 2/2001 | Cohen | .......................... | 433/92 |
| 6,203,321 B1 * | 3/2001 | Helmer et al. | ................ | 433/95 |
| 6,220,859 B1 * | 4/2001 | Hoffman | ...................... | 433/91 |

* cited by examiner

*Primary Examiner*—Melba N. Bumgarner
*Assistant Examiner*—Jonathan Werner
(74) *Attorney, Agent, or Firm*—James L. Jackson

(57) ABSTRACT

A disposable cushioned aspirator which forms part of a dental or medical aspirating system. The disposable cushioned aspirator appliance described herein is intended principally to be used in dental and medical procedures where body fluids and rinse water is evacuated from the site of a procedure. An elongate tubular element has a connection end and a patient end. The patient end is exteriorly lined with a layer of soft cushioning material such as a soft thermoplastic elastomers, styrene based polymers, rubber or a porous polymer foam material to define an aspirator tip that protects the soft tissues in and around the mouth of a patient. The soft aspirator tip has external longitudinal pressure relief channels and recessed aspiration openings within the channels for control of aspiration characteristics. The aspirator tube is capable of being manually bent to a desired configuration and has an embedded structural member such as wire extending along its length and being pliable to permit bending and yet of sufficient structural integrity to maintain the aspirator in the desired configuration during use.

16 Claims, 6 Drawing Sheets

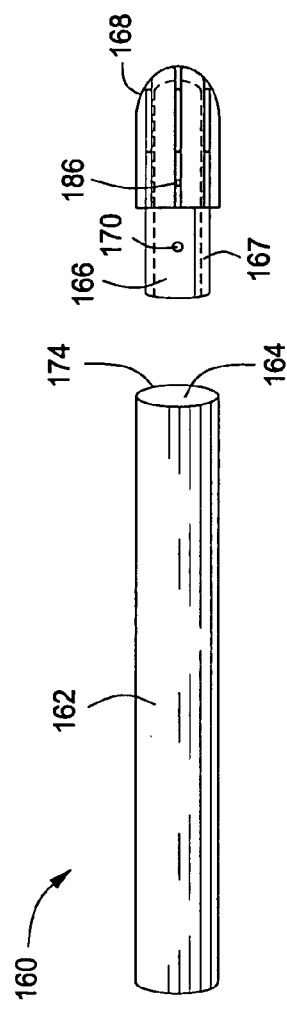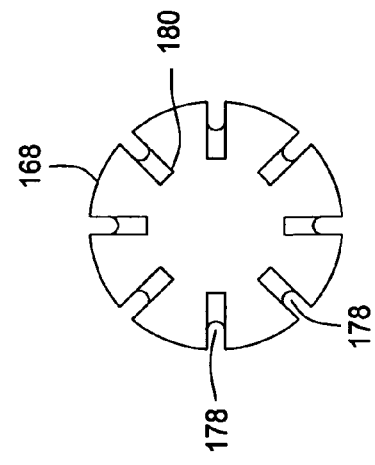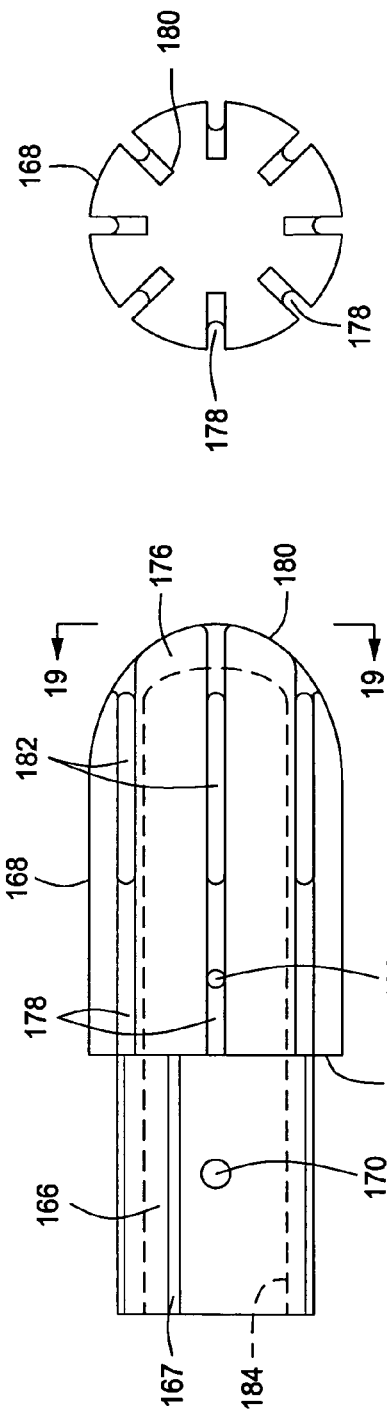

ASPIRATOR HAVING A CUSHIONED AND ASPIRATION CONTROLLING TIP

RELATED PROVISIONAL APPLICATION

Applicant hereby claims the benefit of U.S. Provisional Patent Application No. 60/514,477, filed on Oct. 27, 2003 by Lee A. Mahlmann and entitled "Aspirator Having Cushioned Section".

RELATED APPLICATION

This is a Continuation-in-Part application based on pending application Ser. No. 11/323,876 which was filed by Lee A. Mahlmann on Dec. 31, 2005 and entitled Aspirator Having Cushioned and Aspiration controlling tip and application Ser. No. 10/909,725 which was filed on Aug. 2, 2004 now abandoned by Lee A. Mahlmann and entitled "Aspirator Having Cushioned Tip".

RELATED PATENT

The present invention is related to the subject matter of U.S. Pat. No. 6,068,477, entitled "Foam Cushioned Aspirator", filed on Jul. 6, 1999 by Lee A. Mahlmann and issued on May 30, 2000.

BACKGROUND OF THE INVENTION

1. Field of the Invention

This invention relates generally to tubular appliances such as tubular aspirators, intubation members and the like for use by medical and dental practitioners, including all dental specialties, for suction enhanced removal of fluid or drainage of fluid from the immediate region of a medical or dental procedure. More particularly, the present invention concerns an aspirator for aspiration of fluids, including body fluids such as blood, saliva, other fluids such as rinse water and the like, as well as fluid entrained solids and other fluid-like materials from a region of interest, such as the oral cavity or a body incision or wound. The present invention also concerns a cushioned tubular appliance for substantially eliminating the potential for aspiration of soft flaccid tissues into aspirator openings and simultaneously protecting such tissues from being pinched or otherwise damaged by hard portions of an aspirator tube. This invention also concerns tubular cushioned intubation members that can be configured for efficient use by surgeons for drainage of fluid from a surgical site. Even more particularly, the present invention concerns the provision of a tubular aspirator having a terminal section provided with a soft, cushioned external aspirator layer for contact with body tissues at a specific aspiration site to prevent damage to body tissues and to promote the general comfort of the patient. The present invention also concerns a tubular aspirator having a terminal section provided with a cushioning external layer forming an aspirator tip that defines a plurality of contoured fluid transfer openings that may be of elongate, round or other suitable configuration, having sufficient cross-sectional dimension for optimum transfer of fluid and being of sufficiently small dimension to minimize the potential for ingress of flaccid tissue into the openings during aspiration activity. The present invention also concerns the provision of a soft and pliable aspiration or saliva or liquid ejection tip that is designed for use during high speed aspiration of liquid and debris from a site via the use of very strong suction and which is designed to be secured by glue or any suitable agent to a tubular aspiration member.

2. Description of the Prior Art

While aspirator devices are used in a wide variety of medical and dental applications, to promote easy understanding of the present invention it is discussed herein particularly as the invention is employed for oral aspiration in the field of dentistry, including orthodontics. The present invention also has application in the field of surgery. For example, the present invention also has application as an intubation member that can be configured by a surgeon during a surgical procedure for efficient drainage of fluid from a surgical site and can be re-configured by the surgeon or nursing personnel as needed to promote efficient drainage of body fluid. The tissue inside the human mouth and lip area around the mouth and also boney areas within the oral cavity are very sensitive and can be easily damaged when aspiration occurs and when an aspirator comes into contact with such tissues. In most dental procedures, a tubular saliva ejector or aspirator is connected to a source of suction and is used to remove the fluid that is typically present and thus dry the mouth so that a dental or medical procedure can be carried out without the inconvenience of a wet field. The problem with most tubular saliva ejectors or aspirators is that they are typically composed of a hard, non-forgiving plastic or metal and define a large diameter end opening through which aspiration occurs. When positioned under the tongue or in the labial vestibule of a patient's oral cavity, the saliva ejector aspirates saliva, blood, and unfortunately also aspirates the soft, flaccid, easily damaged oral tissues that are present. The suction of aspiration can cause the tissue to be pulled into the aspirator opening, blocking the opening and subjecting the soft tissue to significant vacuum induced force. Once the tissue is aspirated into the holes of a saliva ejector a "blood blister" is often created very quickly. When the aspirator tube is removed from the mouth as suction is being applied, pulling it away from the patient's tissue is very painful to the patient and often causes the blood blister to remain. Not only does a hard plastic or metal aspirator cause discomfort inside the mouth of a patient but often pinches the lower lip against the lower teeth. This occurrence typically causes pain to the lip and can actually cause bruising of the lip. The discomfort that a hard aspirator can cause during a dental procedure can greatly affect the outcome of the dental procedure. An uncomfortable patient is not as cooperative as a comfortable one. The end result can be less than ideal.

At times high speed aspiration is employed to clear a body site such as an oral cavity or surgical site. In such case a very strong suction is often employed, thus potentially creating a condition where flaccid or soft body tissues can be easily damaged by the wide differential pressure condition of high speed aspiration. High speed air movement during aspiration can draw soft or flaccid body tissue into the opening or openings of an aspirator and can substantially instantly produce a blood blister or other tissue damage. It is desirable therefore to provide an aspirator tip that is designed for high speed aspiration, provides a soft and pliable tip geometry for contact with body tissues and minimizes the potential for tissue damage during high speed aspiration.

SUMMARY OF THE INVENTION

The tubular aspirator appliance of the present invention is designed to be the initial or fluid inlet section of a dental or medical aspirating system. The aspirator appliance is designed, for example, for an end portion of the aspirator to be inserted into a patient's mouth, with suction being applied to remove collected saliva/water by means of suction. The aspirator appliance is attached to a remote central vacuum unit by way of a flexible tube having a conventional vacuum line connection for medical and dental operators. The present invention is unique in that it has a skeletal structure made up of a flexible polymer tube in which a rather stiff but pliable wire is embedded to allow the aspirator to be bent or otherwise formed to a specific shape for a specific dental or medical procedure and to remain so bent until subsequently bent to another shape. An end portion or section of the skeletal polymer tube is provided with a cushioning covering composed of a soft rubber or rubber-like cushioning material or a non-toxic, open cell, foam material that protects not only the soft tissue within the mouth but all tissues around the mouth. The external cushioning covering of the aspirator device of the present invention has cushioning material that extends along a desired section of the appliance and provides a cushioning end that extends beyond the inlet end of the aspirator tube and defines a plurality of fluid transfer openings that provide for efficient aspiration of fluid and minimize entry of flaccid tissue into the fluid transfer openings during use. The aspirator has an end connection part that is attached to the central vacuum tubing by means of a conventional medical/dental vacuum line connection. Thus the cushioning effect of the aspirator of this invention protects not only the soft tissue within the mouth but also the teeth and lips of the patient.

The aspirator consists of a desired length of flexible plastic tube, strong enough to withstand strong suction without collapsing. The aspirator tube has a wire imbedded in it and extending longitudinally, substantially the full length of the tube. The embedded wire allows the aspirator tube to be manually bent and formed to any desired shape as needed for different dental or medical procedures. Under circumstances where the aspirator tube is not intended to be deformed by bending, the aspirator may be manufactured without an embedded wire or structural member. A desired section of the aspirator tube, which may be the aspirator tip, or even a major section of the aspirator tube, is covered at least partially by a soft cushioning material that is located for contact with the oral tissues of the patient and protects the oral tissues, the lips and the teeth of a patient from aspirator contact injury. The tip of the aspirator defines external longitudinal pressure relief grooves, with one or more fluid transfer openings located within each of the pressure relief grooves and communicating with a chamber that is defined within the tip beyond the end of the aspirator tube. The aspirator tube has a small connecting section that releasably connect the aspirator to a vacuum tube extending from the central vacuum source of a dental or medical operatory.

The formable-cushioned tip aspirator of the present invention designed for multiple sizes and tip designs can eliminate the problems caused by a hard plastic or metal aspirator. A soft, cushioned outer covering of foam or rubber-like material at the aspirator tip covers a portion of the tubular aspirator and provides an aspiration end for contact with the tissues of the patent. The aspirator end defines a plurality of fluid transfer openings having optimum cross-sectional dimension and contoured configuration for efficient fluid transfer and with the fluid transfer openings designed so as not allow the aspirator to impinge, aspirate, or bruise any tissue in or around the oral cavity of a patient. The fluid transfer openings may be of elongate, round, oval or of other suitable configuration and are oriented in peripherally spaced relation so that one or more of the openings remain unobstructed to permit suction flow even when the aspirator tip is placed in a small or tight region of the oral cavity. This aspirator tip design is not only optimized for use in dentistry but can also be utilized in many medical applications. It is gentle to all soft tissues that it contacts and yet is efficient for fluid removal from the site of a dental or medical procedure.

The resilient covering of the aspirator tube has a rounded end portion that extends beyond the inlet end of the aspirator tube. This rounded end portion defines a plurality fluid transfer openings of elongate, round, oval or any other suitable cross-sectional configuration having a sufficiently minimal width to minimize the potential for suction induced movement of flaccid tissues into the fluid transfer or aspiration openings and have a length, width that or other dimension that is sufficient to define fluid transfer openings of adequate cross-sectional dimension for efficient aspiration of fluid and yet fluid transfer openings that are sufficiently small that flaccid tissue will not tend to enter and block the openings. Further, the plurality of fluid transfer openings are spaced about the rounded end portion of the tip and oriented to ensure that one or more of the fluid transfer openings will remain open for fluid aspiration even when the tip of the aspirator is placed within a small or tight region of the cavity being subjected to aspiration. When the aspiration openings are defined in or by open call foam material the openings can effectively take the form of a multitude of foam material openings and interstices that essentially permit aspirated fluid to be forced through the foam material by the vacuum source.

To provide the practitioner with the capability to achieve desired aspiration control aspirator tips defining different numbers and locations of aspiration or fluid transfer openings or having openings that are sized for the character of aspiration that is intended. A an aspirator tip is provided having a tip body that defines a plurality of longitudinally oriented external pressure relief channels. Intermediate the length of the external pressure relief channels there is defined an elongate, opening or recess having its bottom surface defined by a membrane. For aspiration control, the membrane defines a plurality of aspiration openings that are sized as desired to accomplish efficient aspiration of fluid from a body site while minimizing the potential for suction actuated movement of flaccid body tissue into the aspiration openings. The fluid transfer openings may simply be located at the bottom portions of the pressure relief channels. Selected pressure relief channels may be provided with one or a plurality of fluid transfer openings and these openings may be of circular or elongate configuration and may be of the same or of different dimension as needed for the character of aspiration that is desired. Location of the fluid transfer openings at the bottom of the pressure relief channels ensures that flaccid oral or body tissues of a patient will not be drawn to the point of blocking the fluid transfer openings.

In the case where high speed aspiration is desired an aspirator tube of relatively large internal diameter and composed of a relatively stiff polymer tubing is often employed. For example a large polymer tube having an external diameter in the range of from about 0.90 centimeters to about 1.30 centimeters and an internal diameter in the range of from about 0.70 centimeters to about 0.80 centimeters. A soft aspirator tip for high speed aspiration is provided with a reduced diameter connection section which is sized to be received and secured by glue or bonding material within the polymer tubing of a high speed aspirator. The head of the aspirator tip defines a shoulder that engages the circular end to the tube and thus establishes the desired position of the aspirator tip relative to an end of the tubular member. The soft high speed aspirator tip is preferably composed of a soft rubber-like polymer material that protects the mouth and oral cavity tissues of a patient from damage during aspiration. The tip defines a plurality of longitudinal suction relief slots, with elongate aspiration openings being located within each of the suction relief slots. The aspiration openings and suction relief slots each define fluid flow areas that, when combined, substantially equal or exceed the cross-sectional dimension of the internal flow passage of the tubular aspirator member.

For high speed aspiration an alternative tip design is provided wherein a soft tip is provided with a reduced diameter tubular connector which is received and secured within the inner flow passage of a polymer tube which is intended to be grasped by a practitioner for aspirator manimulation. The head of the aspirator tip defines a shoulder that engages the circular end to the tube and thus establishes the desired position of the aspirator tip relative to an end of the tubular aspirator member. The head portion of the aspirator tip defines a smoothly curved end which is oriented in angular relation to the longitudinal center-line of the tip, thus providing an aspiration opening that exceeds the annular dimension of the flow passage of the tubular member. The head of the aspirator tip is also provided with one or more suction relief holes that communicate with the internal suction passage that is defined by the tip. These suction relief holes minimize the potential for tissue damage under circumstances where the end opening of the aspirator tip becomes completely blocked by the tissue of the patient.

BRIEF DESCRIPTION OF THE DRAWINGS

So that the manner in which the above recited features, advantages and objects of the present invention are attained and can be understood in detail, a more particular description of the invention, briefly summarized above, may be had by reference to the preferred embodiment thereof which is illustrated in the appended drawings, which drawings are incorporated as a part hereof.

It is to be noted however, that the appended drawings illustrate only a typical embodiment of this invention and are therefore not to be considered limiting of its scope, for the invention may admit to other equally effective embodiments.

In The Drawings

FIG. 1 is a side view of a formable cushioned aspirator having a cushioned end section or tip and representing the preferred embodiment of the present invention, the aspirator being shown in the substantially straight non-bent form thereof;

FIG. 2 is a longitudinal sectional view of the formable-cushioned aspirator of FIG. 1;

FIG. 3 is a sectional view taken along line 3-3 of FIG. 2;

FIG. 4 is a sectional view taken along line 4-4 of FIG. 2 and showing the relationships of the flexible tube element and the structural wire;

FIG. 5 is an elevational view showing the formable cushioned aspirator of the present invention being bent to a curved form particularly for dental application;

FIG. 6 is an end view taken along line 6-6 of FIG. 2 and showing the patient end or tip of the formable aspirator device;

FIG. 7 is a partial side elevational view of an alternative embodiment of the present invention, showing the cushioned tip thereof having fluid transfer openings of oval configuration;

FIG. 8 is a partial side elevational view of another alternative embodiment of the present invention, showing the cushioned tip thereof having fluid transfer openings of round configuration;

FIG. 9 is a partial side elevational view of another alternative embodiment of the present invention, showing an aspirator tip being composed of open cell polymer foam material which defines interstices that collectively define the fluid transfer passage system of the aspirator;

FIG. 10 is a sectional view taken along line 10-10 of FIG. 9;

FIG. 11 is a partial side elevational view showing an alternative embodiment of the present invention incorporating a tubular element having a formable structural member embedded therein and having a resilient tip member defining a rounded end having external fluid channels or grooves and having a single end opening;

Figure 12:
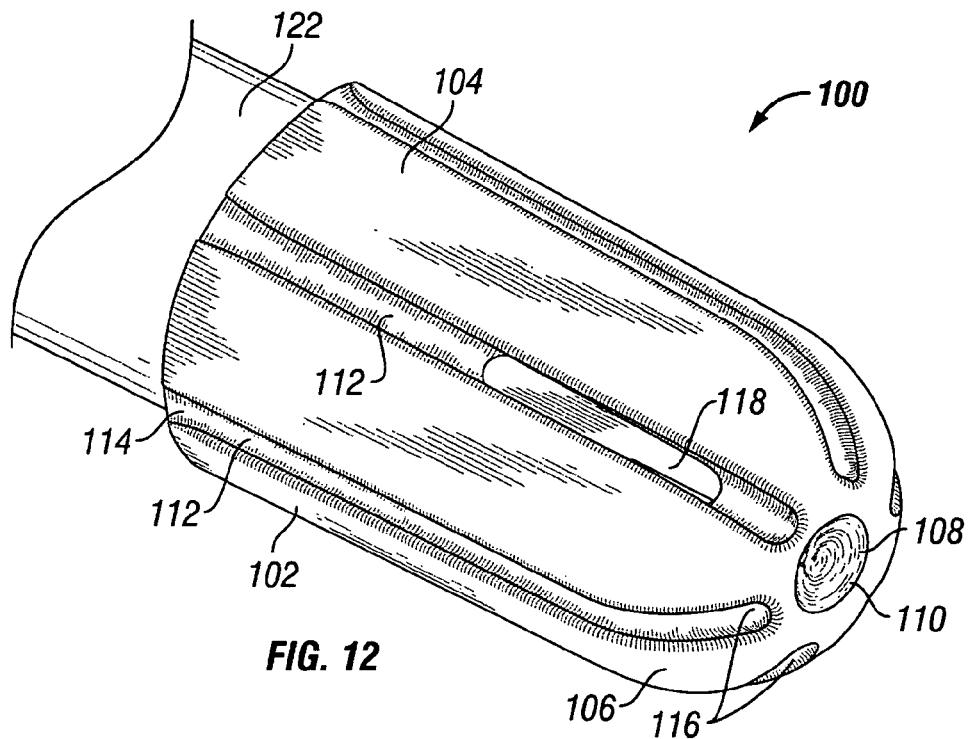
Figure 13:
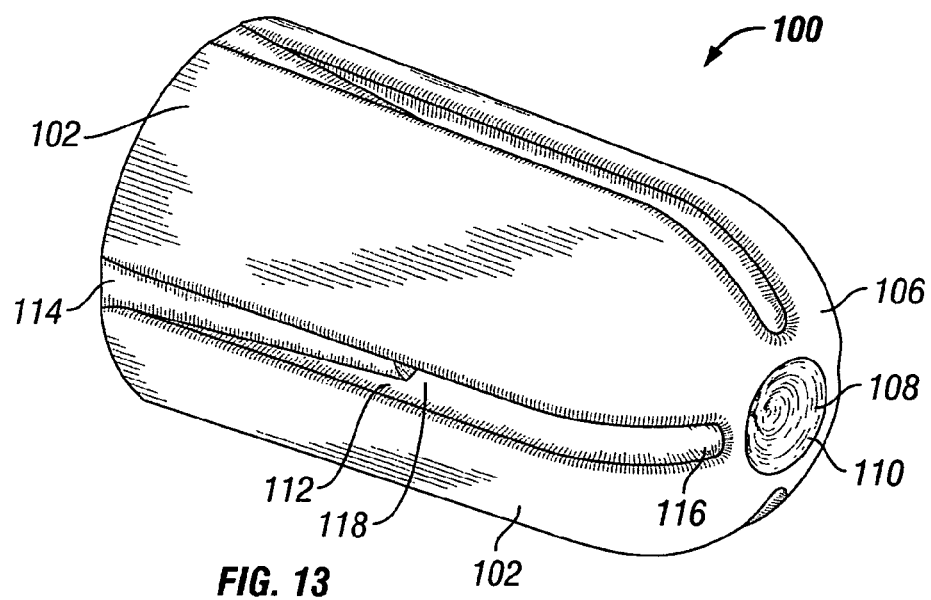
Figure 14:
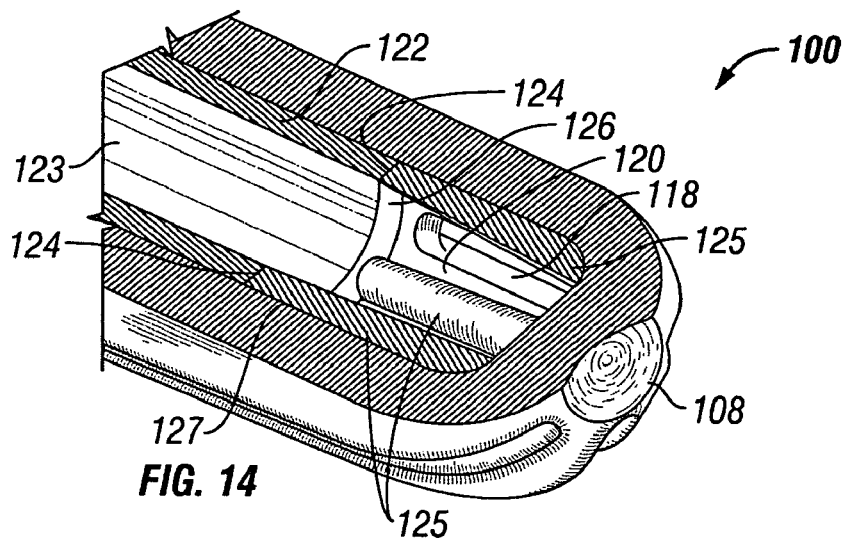
Figure 15:
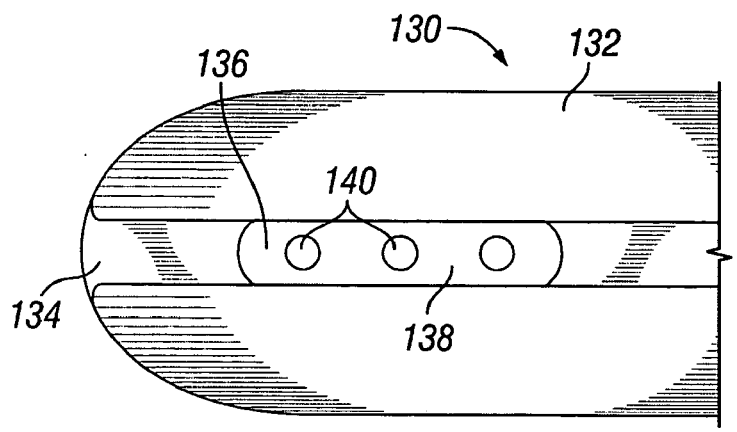
Figure 16:
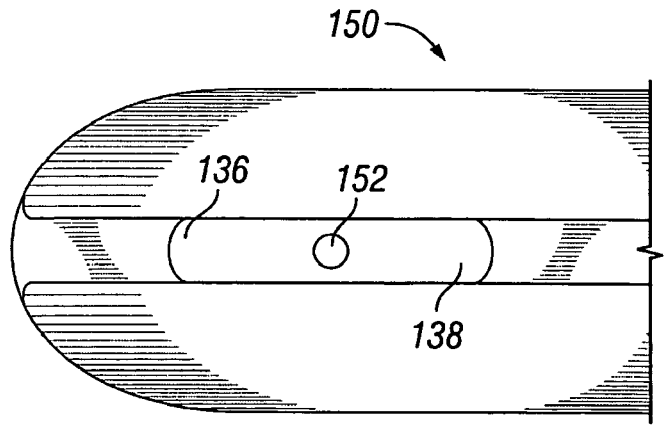

FIG. 12 is an isometric illustration showing an aspirator tip representing the preferred embodiment of the present invention;

FIG. 13 is another isometric illustration showing the aspirator tip of FIG. 12;

FIG. 14 is an isometric illustration shown partially in longitudinal section and illustrating the internal geometry of the aspirator tip of FIG. 12 with an end of an aspirator tube of FIGS. 1-11 seated therein;

FIG. 15 is a partial elevational view showing the external configuration of an aspirator tip embodying the principles of the present invention and showing a plurality of aspiration control openings enabling desired characteristics of aspiration; and FIG. 16 is a partial elevational view showing the external configuration of another aspirator tip of the present invention having a single aspiration control opening within each external groove for control of the characteristics of aspiration.

Figure 20:
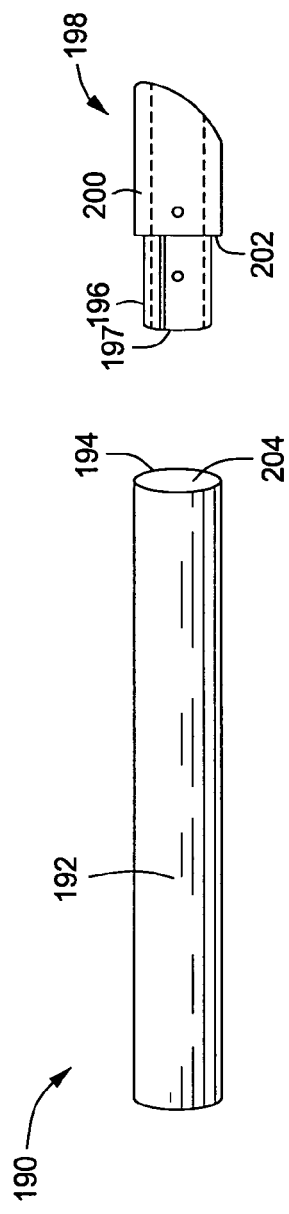
Figure 22:
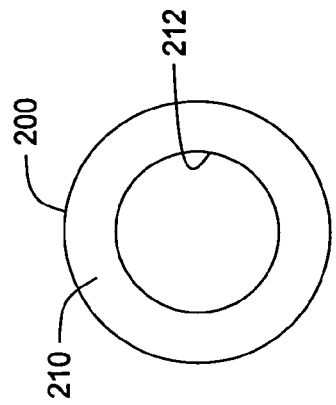
Figure 21:
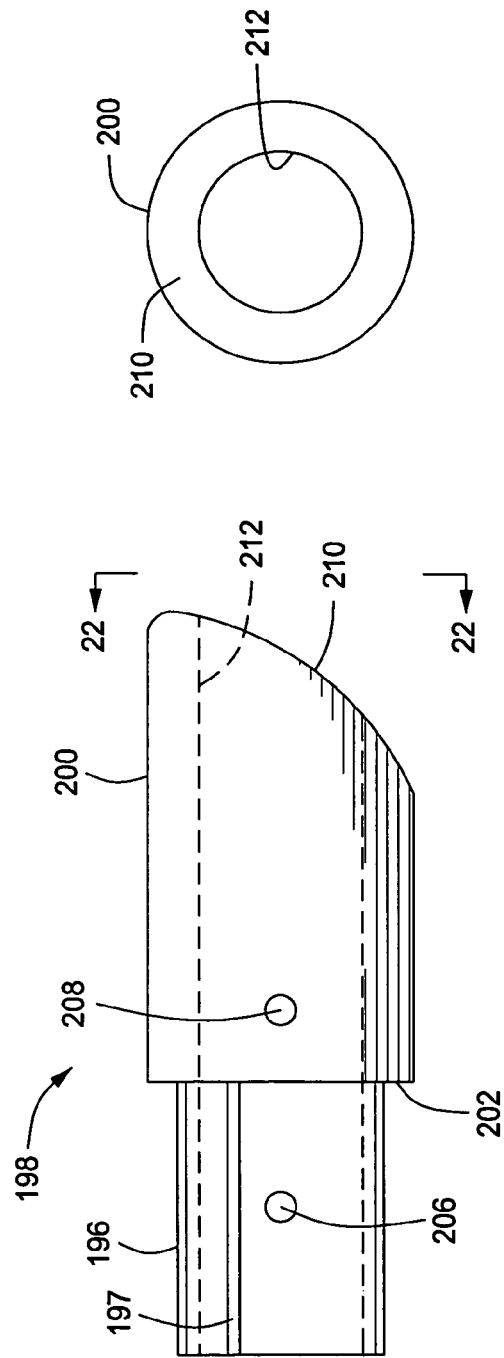

FIG. 17 is an exploded elevational view showing the aspiration tube and aspirator tip of a high speed aspirator or ejector assembly embodying the principles of the present invention;

FIG. 18 is an elevational view showing the aspirator tip of the high speed aspirator assembly of FIG. 17;

FIG. 19 is an end elevational view taken along line 19-19 of FIG. 17, showing the aspirator tip geometry in detail;

FIG. 20 is an exploded elevational view showing the aspiration tube and aspirator tip of a high speed aspirator or ejector assembly representing an alternative embodiment of the present invention;

FIG. 21 is an elevational view showing the aspirator tip of FIG. 20 in detail; and FIG. 22 is an end elevational view taken along line 22-22 of FIG. 21, showing the aspirator tip geometry in detail;

DETAILED DESCRIPTION OF PREFERRED EMBODIMENT

Referring now to the drawings and first to FIGS. 1-5, a disposable formable cushioned aspirator representing the preferred embodiment of the present invention is shown generally at 10. The formable-cushioned aspirator 10 consists of an elongated hollow flexible tube 12 preferably composed of a suitable polymer or rubber and defining a generally cylindrical external surface 14 extending substantially the entire length thereof. The elongate flexible hollow tubular element 12 has a central flow passage 13 and defines a connector end section 16 to which is typically assembled a suction tube connector (not shown) that enables attachment of the formable cushioned aspirator 10 to the usual flexible tube of a central vacuum pump or vacuum system (not shown). The flexible tubing and the suction tube connector may be of conventional nature, but preferably it is fixed to the connector end section 16 of the flexible hollow tubular element 12. This feature permits an aspirator to be releasably assembled to a suction tube so that it can be easily removed and disposed of in a manner that prevents any potential for cross-contamination between patients. The connector end section 16 of the flexible hollow tubular element 12 of the aspirator can range in size for example from about 10 mm to about 35 mm or it may be of smaller or greater dimension if desired.

Within the flexible hollow tubular element 12 is an embedded a formable structural member such as a fairly rigid wire 18 which is preferably composed of soft and pliable metal such as stainless steel, mild steel, aluminum alloy or any suitable non-metal material that can be bent and take a set so that it remains in its bent configuration. The formable structural member 18 within the, aspirator permits the aspirator to be bent by the practitioner during a dental or surgical procedure to conform to a specific configuration for efficient use (FIG. 5) and permits the configuration of the aspirator to be altered as desired. The wire size is of sufficient diameter that it can be easily manually bent by a dental or medical practitioner or assistant to perform its necessary configuration retaining function, but the wire is not so large as to inhibit the suction capacity of the flexible hollow tubular element 12. The structural integrity of the stainless steel wire 18 is sufficient to permit the cushioned aspirator to be manually bend to a desired configuration and to maintain the desired configuration during use. In some applications where the aspirator tube does not need to be bent to a desired configuration and remain bent, the formable structural member or wire 18 can be eliminated, leaving the flexible hollow tubular element 12 to form the basic structure of the aspirator. In this case it should be noted that the flexible hollow tubular element 12 will have sufficient flexibility that it can be manually flexed to a desired configuration to accomplish a desired task. When the manually applied flexing force is dissipated, the flexible hollow tubular element 12 will return to its original, substantially straight configuration due to its elastic memory. The flexible hollow tubular element 12 can have an inside diameter ranging from a minimum of about 3 mm to whatever size meets the needs of the practitioner.

To provide the aspirator structure with a cushioning capability in the region of its contact with the tissue of the patient and to facilitate efficient vacuum induced fluid retrieval, the flexible hollow tubular element 12 is provided with a flexible cushioning tip shown generally at 20. The flexible cushioning tip 20 is preferably composed of a soft flexible polymer or rubber material or may be composed of a polymer foam material as desired. The flexible cushioning tip 20 can be molded onto the suction or fluid transfer end 22 of the flexible hollow tubular element 12 if desired or it can be manufactured as a separate component and placed in assembly on the tubular element 12. The length of the flexible cushioning tip 20 may vary from a minimum length of about 4 cm to a maximum of about 12 cm or more. If desired, the flexible tubular tip element may extend virtually the entire length of the tubular element 12. The thickness of the flexible cushioning tip 20 covering the hollow plastic tube 12 may range from about 1 mm to about 10 mm or whatever thickness is needed to meet the cushioning effect that is desired. The normal thickness range of the flexible cushioning tip 20 is from about 1 mm to about 3 mm. The overall length of the cushioned aspirator 10 can be variable depending on dental or medical procedure it is being used for. For a dental procedures the average length of the cushioned aspirator 10 would range from for example from about 90 mm to about 150 mm.

Figure 1:
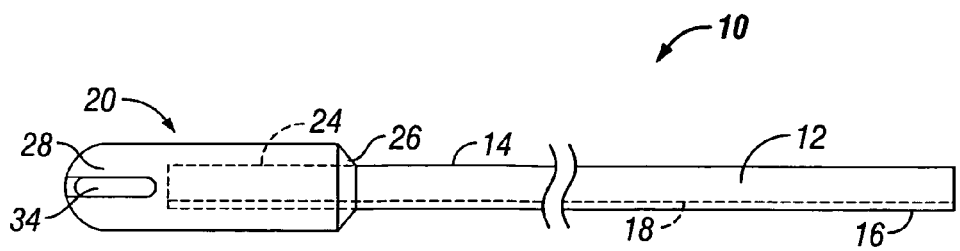
Figure 2:
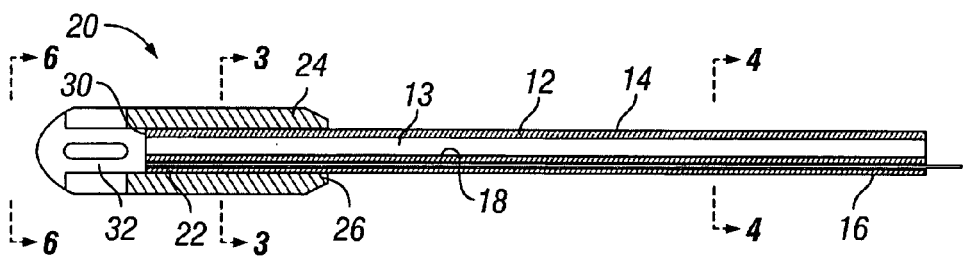
Figure 3:
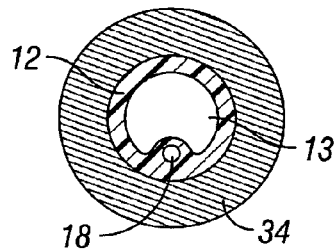
Figure 4:
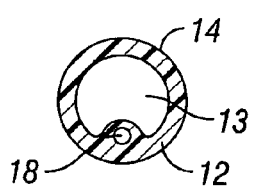
Figure 5:
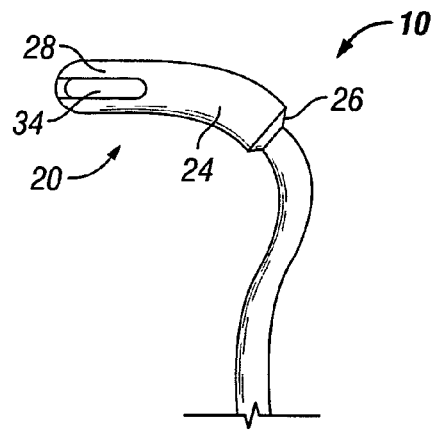
Figure 6:
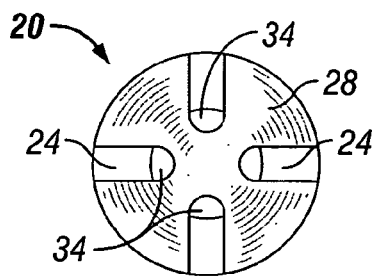

The flexible cushioning tip 20 of the patient end, i.e., suction or fluid transfer end 22 of the aspirator, as shown in FIGS. 1-6, through which saliva/blood/water and debris is aspirated into the flexible hollow plastic tube 12. The flexible cushioning tip 20 is of tubular form defining a generally cylindrical wall 24 that fits closely about the external generally cylindrical surface 14 or is formed onto the generally cylindrical wall 24 such as by molding. The wall 24 of the flexible cushioning tip 20 terminates at one end with a tapered end section 26 that merges the flexible cushioning tip with the external cylindrical surface 14 of the flexible hollow plastic tube 12. This feature minimizes the potential for fluid or debris to be retained at the juncture of the flexible cushioning tip with the flexible hollow plastic tube 12.

flexible cushioning tip 20 defines a closed, rounded distal end 28 that projects beyond the remote or distal end 30 of the flexible hollow plastic tube 12 and thus, with the flexible hollow plastic tube 12, defines a fluid transfer chamber 32 that is in fluid communication with the central flow passage 13. The closed rounded distal end 28 of the flexible cushioning tip 20 defines a plurality of fluid transfer openings 34 which, as shown in FIG. 6 are oriented in outward radiating fashion, there being shown four radiating fluid transfer openings 34 in the Figure. It should be borne in mind however, that the closed rounded distal end 28 of the flexible cushioning tip 20 need only define a single fluid transfer opening in order for vacuum induced fluid aspiration to occur. The outwardly radiating fluid transfer or liquid aspiration openings, which are evenly distributed about the periphery of the closed rounded distal end of the flexible cushioning tip, assure that at least one of the fluid transfer openings will remain open even when the flexible cushioning tip is inserted into a close or tight region within a body cavity of a patient. This feature effectively minimizes the potential that all of the fluid aspiration openings will become simultaneously blocked by flaccid tissue of the patient and allows efficient vacuum induced flow of air and fluid to continuously occur even though some of the fluid transfer openings may become blocked. Thus the vacuum induced force that is applied to some of the flaccid tissue remains low, even though efficient aspiration occurs; thus the flaccid tissue is not subjected to sufficient vacuum induced force that blood blisters or aspirator induced pain will tend to occur.

The aspirator construction of the present invention is shown in three different forms. FIGS. 1-6 show the flexible cushioning tip 20 being provided with multiple fluid transfer or liquid aspiration openings 34 that are evenly spaced about the periphery of the closed rounded distal end 28 and are oriented in outwardly facing radiating relation. The fluid transfer openings range in size from about 0.5 mm to about 2 mm or more across or in diameter or the size of the fluid transfer openings may be greater or smaller to accommodate the size of the aspirator and its application and/or to accommodate the character of use that is desired by a practitioner. When the fluid transfer openings are of elongate, essentially slotted form, they have a transverse dimension in the range of about 0.5 to 2 mm and a length of from about 1 cm to 1.5 cm or more, and the narrow width thereof is designed to retard entry of flaccid tissue that might otherwise block the openings.

Figure 7:
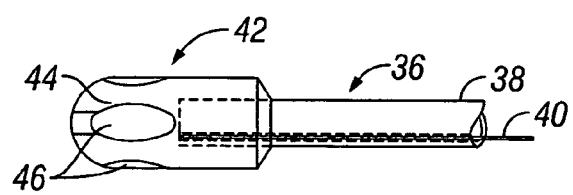

FIG. 7 represents an alternative embodiment of the present invention which shows the distal end portion of an aspirator 36 embodying the principles of the present invention and shows a flexible aspirator tube 38 within which is located a formable structural element 40 such as a wire member. It should be noted that the wire member 40 does not normally extend beyond the end of the flexible tubular element 38, but rather is shown in FIGS. 7, 8, 9 and 11 of the drawings to facilitate ready understanding of this invention. Typically the wire member is embedded within the flexible polymer material of the tubular element and extends from end to end thereof. The flexible tubular element is typically manufactured in long lengths by extruding the polymer material about a length of wire in similar manner to the manufacture of coated electrical wire and cable. Then the long length of tubular material is cut into desired sections having a length that is suitable for use in fluid aspiration and for use during surgical intubation. About the flexible aspirator tube 38 is positioned a flexible cushioning aspirator tip shown generally at 42 having a closed rounded distal end 44 defining a plurality of aspirator openings 46 of oval configuration to allow aspiration of not only saliva, water, and blood, but also fairly large debris particles.

Figure 8:
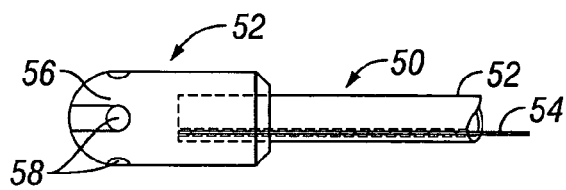

Another alternative embodiment of the present invention is shown generally at 50 in FIG. 8 which shows the distal end portion of a flexible aspirator tube 52 having a formable structural member 40 such as a wire member. A flexible cushioning aspirator tip shown generally at 52 is positioned about the distal end portion of a flexible aspirator tube 54 and defines a closed rounded distal end 56 defining a plurality of fluid transfer or aspirator openings 58 of circular configuration to allow aspiration of fluid from a cavity of interest.

Figure 9:
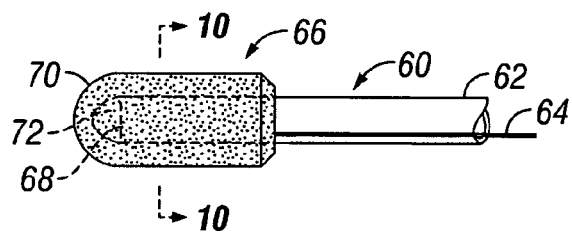

A further embodiment of the present cushioned aspirator invention is shown generally at 60 in FIG. 9 wherein a flexible tubular member 62, preferably composed of a polymer or rubber material, is provided with a formable structural member 64 such as an embedded wire that extends substantially the entire length thereof. A flexible cushioning aspirator tip of tubular form is shown generally at 66 and defines a tubular wall 67 that is composed of a closed cell polymer foam material that may be molded or otherwise positioned about the distal end portion 68 of the flexible tubular member 62. A rounded closed distal end 70 of the flexible cushioning aspirator tip 66, which is integral with the tubular wall 67, defines a multitude of interstices that serve as aspiration passages that permit fluid to be drawn through the flexible cushioning aspirator tip and into an internal fluid transfer chamber 72 and thence through the internal flow passage of the flexible aspirator tube 62 toward the source of vacuum.

Figure 10:
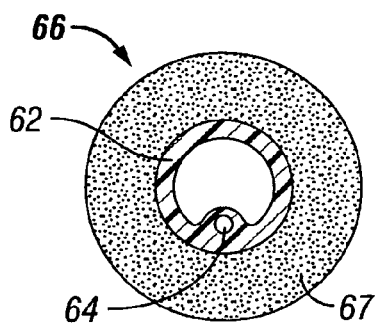

As noted in FIGS. 9 and 10, the tubular foam covering of the aspirator tip extends from about 2 mm to about 4 mm past the patient or distal end 68 of the flexible hollow tube 62 to provide for a cushioned effect when the patient or distal end of the foam-cushioned aspirator is moved into engagement with soft or flaccid tissue of the patient. This feature effectively prevents damage to the soft tissue of the patient if the tissue comes into contact with the external surface of the aspirator tip.

Regarding FIGS. 9 and 10, it should be noted that the foam-cushioned aspirator with a closed foam tip 28 requires that suction be applied through the porous foam cushioning material. The foam in this application would need to be porous enough to allow for suction to occur and to allow typically occurring liquid material to flow through the foam material and into the aspirator tube. Polyurethane foam would best suit this purpose and comes in two types; polyether based and polyester based. The polyether based foam is considered preferable because it has greater flexibility and allows for greater suction/air flow rate.

Figure 11:
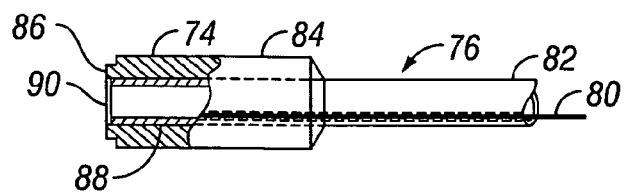

The embodiment of FIG. 11, shown generally at 76 comprises a flexible polymer tubular element 82 having an elongate formable structural member 80 embedded therein and extending along the length thereof. Here again, the elongate formable structural member or wire 80 is shown to extend beyond a portion of the flexible tubular element 82 only for the purpose of simplicity and understanding. In practice, the embedded wire 80 will normally extend from end to end of the flexible tubular element 82, though in some limited circumstances it may be desirable that the wire extend beyond one of the ends thereof. A generally cylindrical tubular tip member 84 having a rather blunt end 86 is placed over an end 88 of the flexible polymer tubular element 82 and, together with the end opening of the tubular element 82, defines a single end opening 90. The end opening 90 is effective for aspiration of fluid material and debris and is also effective for fluid drainage when the formable cushioned tubular appliance is utilized for intubation at a surgical site. It should be borne in mind that the tubular tip element 84 may extend along any suitable length of the tubular element 82, thus it is not intended to restrict the spirit and scope of the present invention to the specific embodiment that is shown.

As shown in FIGS. 12-16, for control of differential pressure and characteristics of aspiration, the preferred embodiment of the present invention is provided with external pressure relief grooves that extend longitudinally of the aspirator tip and further ensure that flaccid tissue is not drawn into the aspiration openings sufficiently to block the openings and cause tissue damage. Additionally, narrow elongate aspiration openings are provided within the longitudinally arranged pressure relief grooves to further protect flaccid tissue from damage during aspiration activity. Within the plurality of narrow elongate radially spaced aspiration openings and well away from the radially outer portions of the pressure relief grooves may be provided narrow elongate membranes which define one or more aspiration control perforations or openings are located that are sized according to the aspiration characteristics that may be desired. These aspiration control openings may be located at any desired region of the narrow elongate membranes and may be of differing size, for example one size for a body surgical procedure and another size for use of an aspirator to clear fluid and debris from the oral cavity.

Referring now to FIGS. 12 and 13, an aspirator tip representing the preferred embodiment of the present invention is shown generally at 100 and includes a tip body 102 defining an elongate generally cylindrical or slightly tapered external tip body surface 104 which merges smoothly with a curved or rounded distal end surface 106. The aspirator tip body is preferably composed of a soft rubber or rubber-like polymer or a porous or non-porous polymer foam material to provide for cushioning when the aspirator tip is brought into contact with the body or oral cavity tissue of a patient. Centrally of the distal end surface 106 is defined a surface 108 which may be in the form of a depression or a flat or slightly protruding surface which is typically defined by removal of a sprue as the result of an injection molding process. The surface 108 has an essentially circular transition 110 with the curved or rounded distal end surface 106, thus providing for patient comfort when the tip geometry is in contact with the body tissue of a patient. In the alternative or in addition to the lateral fluid transfer aspiration openings a centrally located fluid transfer passage may extend from the rounded end of the aspirator tip into the internal aspiration chamber of the tip. Thus, the aspirator tip may have only lateral openings, lateral openings and a centrally located end opening or simply a single end opening as determined by the character of the aspiration that is intended by a dental practitioner or a medical practitioner.

A plurality of external pressure or aspiration relief channels 112 are defined in substantially evenly radially spaced relation in the external surface geometry of the aspirator tip 100 and extend substantially longitudinally of the tip structure. Each pressure or aspiration relief channel has a proximal end 114 and a distal end 116. The proximal end of each pressure or aspiration relief channel is flared and merges with the external proximal end surface of the tip. The pressure relief channels increase in depth from the proximal end to the distal end such that the proximal ends of the pressure relief channels substantially merge with the external tip body surface 104 and at the distal end the pressure relief grooves each have gently curved merger with the rounded distal end surface 106 of the tip. Each of the pressure or aspiration relief channels also merge smoothly with the external tip body surface 104 thus ensuring that no sharp edges are presented for contact with the body tissue of a patient. The pressure or aspiration relief channels also increase gradually in depth from their proximal ends to their distal ends and define bottom surfaces that are somewhat planar and tapered near the proximal ends and transition to curved or of essentially cylindrical configuration at their distal ends. The increased depth of the pressure or aspiration relief channels at their distal ends permits significantly greater aspiration induced flow of fluid through the distal ends of the pressure relief channels and into laterally oriented aspiration openings 118. The aspiration openings 118 are located within the pressure or aspiration relief channels and establish communication with an aspiration chamber 120 that is defined by the interior of the tip body as is best shown in the sectional view of FIG. 14. The aspiration chamber may also be referred to herein as a fluid transfer chamber since its purpose is to transfer fluid, including air and debris from the fluid transfer openings into the flow passage of the elongate tubular member.

As is evident from FIG. 14 it is deemed appropriate to ensure that the aspirator tube 122 is accurately seated within the aspirator tip 100 so that the lateral aspiration openings 118 are not blocked by unusually deep seating of the aspirator tube. Accordingly, internally of the aspirator tip body 102 is provided at least one and preferably a plurality of seating shoulders 124 that are defined by the ends of a plurality of internal ribs 125. The seating shoulders are engaged by the distal end 126 of the aspirator tube 122 when the aspirator tip is assembled to the tubing, thus providing positive stops for the end of the aspirator tube. The seating shoulders 124 may simply be defined by the internal geometry of the aspirator tip body or in the alternative they may be defined by an insert 126 that is seated within the internal cavity of the aspirator tip body. When inserts are employed, such as shown at 126, inserts of differing length or having stop shoulders differently located may be provided, thus providing a medical or dental practitioner with the capability of selectively adjusting the aspiration characteristics of an aspiration system according to the needs of the patient or the procedure being accomplished. When the seating shoulders are simply defined within the aspirator tip by the internal geometry of the tip body the lateral or longitudinal aspiration or fluid transfer openings will be defined by the tip body. In the alternative, when the seating shoulder is defined by an insert positioned within the tip body the lateral or longitudinal aspiration or fluid transfer openings may be defined by the insert or the tip body or both the insert and tip body acting in concert.

For cushioning capability the aspirator tip is typically composed of soft, pliable or resilient rubber or rubber-like material to provide the desired cushioning capability for protection of the soft and the boney tissues of the oral cavity and for protection of a surgical site from the trauma that might be caused by a typical hard plastic aspirator. The material of the aspirator tip is sufficiently soft that it is easily deformed by mechanical force, such as when manual force is applied to the aspirator when it is in contact with body tissue. The capability of being mechanically deformed provides protection against damage to the body tissue by forces that are manually applied to the aspirator assembly. When aspiration is in progress and the suction or negative pressure is significant, blockage of the aspiration or fluid transfer openings can cause a soft rubber-like aspirator tip to collapse, thus blocking or significantly reducing the fluid transfer capability of the aspiration openings of the tip. In the event of suction induced collapse of the aspirator tip of FIG. 14, the internal ribs 125 will come into tip body supporting contact and will support the tip body in a condition with the aspiration openings 118 remaining open. Additionally, the internal ribs 125, when in contact due to suction induced tip collapse, define internal flow channels within the tip that conduct flowing body fluid from the aspiration openings, through the tip body and to the flow passage 123 of the aspirator tube 122. Thus, even in the event of suction induced tip collapse, the aspirator assembly will be maintained in condition for suction actuated removal of body fluid and debris. If desired, the internal ribs may be defined by the soft resilient material of the aspirator tip or when an insert 127 is located within the tip the internal ribs may be defined within the insert. The insert 127 may be composed of a material that is yieldable but provides sufficient structural integrity for supporting the aspirator tip against a tendency to become deformed by the force of suction to the extent that the fluid transfer openings become blocked.

Of late it has become the practice particularly in the field of dentistry to provide polymer materials for patient contact having a variety of pleasing colors and to provide such materials with a pleasing taste as well. For this reason it is intended that the aspirator tip of the present invention have the capability of being impregnated with one or more coloring agents and/or one or more flavoring agents.

Referring now to FIGS. 15 and 16, it may be desired to provide the practitioner with the capability to achieve desired aspiration control simply by providing aspirator tips defining different numbers and locations of aspiration or fluid transfer openings or to provide openings that are sized for the character of aspiration that is intended by a dental practitioner or a medical practitioner. As shown in FIG. 15 an aspirator tip is shown generally at 130 having an aspirator tip body 132 that defines a plurality of longitudinally oriented external pressure relief channels 134. Intermediate the length of the external pressure relief channels there is defined an elongate opening or recess 136 having its bottom surface defined by a membrane 138. For aspiration control, the membrane 138 defines a plurality of aspiration openings 140 that are sized as desired to accomplish efficient aspiration of fluid from a body site while minimizing the potential for suction actuated movement of flaccid body tissue into the aspiration openings. Alternatively, it is not necessary that a membrane having fluid transfer openings be provided. If desired, the fluid transfer openings may simply be located at the bottom portions of the pressure relief channels 134. Selected pressure relief channels may be provided with one or a plurality of fluid transfer openings and these openings may be of circular or elongate configuration and may be of the same or of different dimension as needed for the character of aspiration that is desired. Location of the fluid transfer openings at the bottom of the pressure relief channels ensures that flaccid oral or body tissues of a patient will not be drawn to the point of blocking the fluid transfer openings.

The aspiration openings may take the form of a plurality of openings located along the length of the membrane as shown or by membrane openings of differing dimension. It should also be borne in mind that the aspiration openings, though shown as being of circular configuration, may have any desired configuration, such as rectangular, elliptical, triangular, etc. depending on the aspiration characteristics that are desired by the practitioner. The multiple aspiration openings may be defined by the aspirator body itself or in the alternative may be defined by an insert 127 that is seated within the aspirator body. In the alternative, the aspiration opening or openings may simply be located at the bottom of the pressure relief channels and are also positioned so as to be clear of the distal end 126 of the aspirator tube 122.

As is evident from the elevational view of FIG. 16 an aspirator tip shown generally at 150 may be of similar construction as compared with the aspirator tip shown in FIG. 15, with the exception that each of the membranes 138 of the elongate opening or recesses 136 are provided with a single aspiration opening 152 which may be located at anywhere along the length of the opening or recess 136 or membrane 138 and may have a circular configuration as shown or any other suitable configuration. It is only intended that the opening or openings be of suitable dimension and configuration for the character of aspiration that is desired.

The aspirator described may be composed of both solid plastic material and porous or non-porous plastic foam. Both parts can be made from non-toxic polymer materials such as polyurethane, rubber, latex, polyethylene, polyvinyl chloride, or vinyl polymides. Preferably the components of the aspiration system are composed of thermoplastic elastomers (TPE) or styrene based polymers. The materials used to make these parts would be chosen and dimensioned to meet specific operative characteristics as intended by a practitioner. And as mentioned above, the aspirator tip material may be provided in a range of pleasing or suitable colors and may be impregnated with a pleasing flavoring agent. For example, a dental practitioner may prefer an aspirator of a particular dimension and a medical or surgical practitioner may prefer an aspirator of a larger or smaller dimension. It is therefore intended that the spirit and scope of the present invention not be restrictive of any particular dimension that might be chosen by a practitioner. When the aspirator or aspirator tip is colored, the color may be representative of a particular type or dimension for a particular character of aspiration. This feature will provide a practitioner with the capability of visually inspecting a number of aspirators and selecting one by its color which is most desired for a particular purpose.

The polymer foam material covering the hollow plastic tube could, if necessary, be glued or bonded. The foam material will most practically take the form of a sleeve of foam material which is positioned over the external surface of the elongate flexible aspirator tube. In most cases, the tubular foam covering would fit tight enough so glue or bonding material would not be necessary. If glue or bonding material is used to secure the polymer foam material to the elongate flexible tube, it should be of a non-toxic, water insoluable type. It is also envisioned that, according to some manufacturing processes, and within the spirit and scope of the present invention, the polymer foam material could be applied to the elongate flexible tube in an uncured state and permitted to cure in place.

Regardless of the particular embodiments shown and discussed herein, the flexible cushioning tip of the aspirator or intubation tube appliance is provided with a generally cylindrical tubular section that is received by the distal or aspirating end portion of the flexible aspirator tube and may have a length extending substantially the entire length of the aspirator tube or extending over a major portion of the aspirator tube, or extending over only an end portion of the aspirator tube as shown in the various Figures. The length of the flexible cushioning tip is thus determined by the needs of the user.

From the aspirating extremity 42 of the aspirator tube, the aspirator cap defines a semi-pointed or rounded closed distal end having a plurality of fluid transfer or aspirator openings that extend from a location near the distal end of the aspirator tube to the free or distal end of the flexible cushioning tip. As shown in the end view of FIG. 6, the flexible cushioning tip defines four aspirator slots, arranged at an angular spacing of about 90° and having outwardly facing radiating orientation. It should be borne in mind however, that the number of aspirator openings or slots may be greater than four or less than four and may be oriented at any desired angular spacing, such as three aspirator slots arranged at an angular spacing 120° or two aspirator slots arranged at an angular spacing of 180°, for example. For efficient aspiration of fluids, especially in the dental practice, where there is often significant flow of saliva and where a substantially dry field is desired, the combined cross-sectional area of the aspiration slots is preferably substantially equal to the cross-sectional area of the flow passage of the aspirator tube. Also, the aspirator slot orientation, with slots located at virtually all sides of the flexible cushioning tip, minimizes the potential that the aspirator slots can become blocked by flaccid tissue of the patient, such as is found within the oral cavity, and especially within the flexible cushioning tip is present within the labial vestibule or under the tongue of the patient. The fluid transfer or aspirator slots shown in the preferred embodiment of FIGS. 1-6 are of sufficiently narrow and elongate geometry and curve along the curved or rounded end of the aspirator cap, so that the soft tissue of the patient is unlikely to completely bridge and seal all of the aspirator openings. Thus, the suction of the aspirator pump is unlikely to establish a force differential that forces the soft tissue of the patient into the aspirator openings so that the formation of vacuum induced blood blisters is effectively minimized.

The present invention is in the form of an elongate formable tubular appliance that incorporates an elongate flexible tube defining an aspirator or drainage fluid flow passage and having a soft metal wire element embedded within the flexible tube. While the present invention is discussed herein particular as it relates to vacuum enhanced fluid aspiration it is not intended to limit the spirit and scope of the present invention to aspirators. Thus, the term "aspirators" is intended to encompass formable cushioned tubular appliances or elements that can be used for fluid drainage or fluid handling of any other similar character. The soft metal wire element provides sufficient structural integrity to permit the flexible tube to maintain any suitable bend configuration as desired by a dental or medical practitioner. The aspirator tube and the soft metal wire are bent manually to a desired configuration and will retain the desired bent configuration during use. Obviously, the bent configuration of the aspirator tube and its covering of cushioning material may be changed if desired by the practitioner. A cushioning: covering, which is composed of a polymer foam material or a soft rubber or soft rubber-like polymer material is located externally of the aspirator tube and is bent to a desired configuration along with the aspirator tube. The cushioning covering defines a portion that extends along a significant length, i.e., from less than half to greater than half of the length of the aspirator tube according to the needs of the practitioner for the particular procedure that is in progress. Beyond the aspirating end of the aspirator tube the cushioning covering defines a plurality of fluid transfer openings. The exterior cushioning covering is flexible and will bend along with the aspirator tube as it is manually bent by the dental or medical practitioner.

Referring now to FIGS. 17-20, a high speed aspirator assembly is shown generally at 160 which incorporates a hollow tubular member 162 that is preferably composed of a rather stiff polymer material that is suitable for use in connection with dental and surgical applications. The hollow tubular member is of rather large diameter as compared with the tubular members of conventional aspirators and has an external diameter in the range of from about 0.90 centimeters to about 1.30 centimeters and an internal diameter in the range of from about 0.70 centimeters to about 0.80 centimeters. The hollow tubular member can have any suitable internal and external dimension that is suitable for dental and surgical application. For example, tube inside diameters in the range of 8 mm or more and an external diameter of 12 mm or more are commercially available at the present time. The present invention is applicable to any aspirator tube sizes that are or can be used, without departing from the spirit and scope of the present invention. The hollow tubular member thus defines a large diameter flow passage 164 which permits application of high speed suction causing high velocity flow of air and debris laden fluid for rapid evacuation of a dental or surgical site as needed by a dental or surgical practitioner. An end opening of the hollow tubular member 162 defines a receptacle within which is received a generally cylindrical connection section 166 of a high speed aspirator tip 168. As shown in detail in FIGS. 18 and 19 the connection section 166 of the high speed aspirator tip 168 may be provided with an opening 170 that serves as a vent that permits relief for the cement or bonding agent that is employed to secure the connection section 168 of the soft pliable aspirator tip within the end opening or receptacle of the tubular member 162. Either the connection section of the aspirator tip or the internal or external tip connection of the tubular member may define one or more longitudinal grooves 167 which serve as passages to vent excess adhesive to facilitate assembly of the aspirator tip to the tubular member. Alternatively these longitudinal passages may also serve as additional suction or aspiration relief passages to minimize the potential for tissue damage during aspiration. This feature minimizes the potential for hydraulic locking of the cement and permits complete seating of the soft pliable aspirator tip to the hollow tubular member so that an annular shoulder 172 of the high speed aspirator tip establishes intimate engagement with the annular end surface 174 of the hollow tubular member. The annular shoulder 172 is defined by a head portion or section 176 of the high speed aspirator tip which has substantially the same external diameter as that of the hollow tubular member 162.

The head portion or section 176 of the high speed aspirator tip defines a plurality of elongate longitudinal suction relief grooves or slots 178 that extend from the annular shoulder 172 to the smoothly curved end surface 180 of the head portion of the high speed aspirator tip. Within the relief slots the head portion or section 176 of the high speed aspirator tip defines a plurality of elongate longitudinal suction openings 182 that establish communication with an internal cavity 184 that is shown in broken line. The internal cavity establishes a portion of the flow passage of the aspirator assembly. The head portion or section 176 of the high speed aspirator tip may also define one or more suction relief openings 186 which are in communication with the internal cavity 184. The suction relief opening or openings permit suction flow which minimizes the pressure differential responsive force on the tissue in the event that all or most of the suction openings of the tip should become blocked by tissue during aspiration, thus protecting the body tissue from damage.

With reference to FIGS. 20-22 a high speed aspirator assembly representing an alternative embodiment of the present invention is shown generally at 190 which incorporates a large diameter hollow tubular member 192 similar to the hollow tubular member of FIG. 17. The hollow tubular member 192 is preferably composed of a rather stiff polymer material that is suitable for use in connection with dental and surgical applications and defines an internal flow passage of greater dimension as compared with the flow passage of conventional aspirators dental and surgical aspirators. The hollow tubular member 192, like the tubular member 162 of FIG. 17 is designed for connection with aspiration tubing that is of suitable dimension for high speed dental or surgical aspiration.

An end opening 194 of the hollow tubular member 192 defines a receptacle within which is received a generally cylindrical connection section 196 of a soft and pliable high speed aspirator tip shown generally at 198. To assure against hydraulic locking of cement during assembly of the aspirator tip to the tubular element the connection section 196 may define one or more longitudinal relief grooves which, when the tip is in assembly with the tubular member 192, constitutes a vent or relief passage 197 that ensures venting of excess adhesive when the tip is assembled to the tubular member. This vent passage or passages may also serve to for suction relief during aspiration The speed aspirator tip 198 has a head portion or section 200 that has an external diameter substantially equaling the external diameter of the hollow tubular member 192. The head portion 200 defines an annular shoulder 202 that is disposed in intimate engagement with the circular end surface 204 of the hollow tubular member when the soft and pliable high speed aspirator tip 198 is fully seated and cemented to an end of the hollow tubular member. To ensure against hydraulic locking of the aspirator tip during assembly to the hollow tubular member in the presence of uncured liquid cement or bonding agent, the connection section 196 may be provided with a cement relief opening 206 or may be provided with a relief groove permitting escape of some of the cement or bonding agent. The head portion 200 of the aspirator tip 198 may also define one or more suction relief openings 208 which permit suction flow even when the suction openings become blocked by tissue. This feature minimizes the pressure differential responsive force on the tissue, thus protecting the body tissue from potential damage during high speed aspiration. At the suction end of the aspirator head 200 there is defined an inclined, annular end surface 210 that is smoothly contoured to minimize the potential for tissue damage when tissue contact is made during high speed aspiration of a dental or surgical site. The soft and pliable aspirator tip 198 further defines a flow passage 212 which is shown in broken line in FIG. 21. This flow passage is of substantially the same internal diameter as compared with the internal diameter of the hollow tubular member 192.

In view of the foregoing, it is evident that the present invention is one well adapted to attain all of the objects and features hereinabove set forth, together with other objects and features which are inherent in the apparatus disclosed herein.

As will be readily apparent to those skilled in the art, the present invention may easily be produced in other specific forms without departing from its spirit or essential characteristics. The present embodiment is, therefore, to be considered as merely illustrative and not restrictive, the scope of the invention being indicated by the claims rather than the foregoing description, and all changes which come within the meaning and range of equivalence of the claims are therefore intended to be embraced therein.

I claim:

1. A formable cushioned tubular fluid aspiration appliance, comprising:

an elongate tubular element defining a flow passage and having a connection end and a distal end and having sufficient flexibility for bending thereof to a desired configuration, said connection end being adapted for connection to a conventional aspirator suction connection fitting, said distal end defining an opening of said flow passage through which fluid is aspirated;

a flexible cushioning tip composed of soft easily deformable resilient material and having a tubular section being located about said distal end of said elongate tubular element and having sufficient wall thickness to present a cushioned aspirator surface for cushioning contact with body tissue of a patient, said tubular section of said flexible cushioning tip having a proximal end and a curved distal end and defining a flexible and easily deformable chamber wall section extending beyond said distal end of said elongate tubular element and defining an aspiration chamber beyond said distal end of said elongate tubular element; and said flexible cushioning tip defining a plurality of external aspiration relief channels extending longitudinally thereof from said proximal end to said curved distal end and gradually increasing in depth from a minimum depth at said proximal end to a maximum depth greater than said minimum depth at said curved distal end, said deformable chamber wall section defining a plurality of aspiration openings located within said external aspiration relief channels and establishing communication with said aspiration chamber and permitting vacuum induced aspiration of fluid into said aspiration chamber and through said flow passage of said elongate tubular element.

2. The formable cushioned tubular fluid handling appliance of claim 1, comprising:

a length of formable structural material being fixed to said elongate tubular element and extending longitudinally thereof, said length of formable structural material being sufficiently pliable to permit manual bending thereof to a desired configuration and being of sufficient structural integrity to maintain the bent configuration thereof.

3. The formable cushioned tubular fluid aspiration appliance of claim 1, comprising:

a plurality of internal ribs being defined within said flexible chamber wall section of said flexible cushioning tip and coming into tip body supporting contact with one another upon suction induced collapse of said flexible chamber wall section of said flexible cushioning tip and defining fluid flow channels from said at least one aspiration opening to said elongate tubular element.

4. The formable cushioned tubular fluid handling appliance of claim 1, comprising: said plurality of aspiration openings being located in said tubular section of said flexible cushioning tip beyond said distal end of said elongate tubular element and being oriented in substantially evenly spaced outwardly facing relation about said flexible and easily deformable chamber wall section.

5. The formable cushioned tubular fluid aspiration appliance of claim 1, comprising:

said flexible cushioning tip having a connection section being received within said distal end of said elongate tubular element and defining a vent opening cooperating with said elongate tubular element to define a relief passage for venting of excess cement or bonding material during assembly of said flexible cushioning tip to said elongate tubular element and providing for additional suction relief during aspiration.

6. The formable cushioned tubular fluid aspiration appliance of claim 1, comprising:

said chamber wall section of said flexible cushioning tip defining a single fluid transfer opening and having an integral soft and flexible curved distal end providing for cushioning of patient tissue when said distal end of said flexible cushioning tip is caused to contact patient tissue during aspiration.

7. The formable cushioned tubular fluid aspiration appliance of claim 1, comprising:

said longitudinal aspiration relief channels extending from said proximal end of said flexible cushioning tip to a region at least partially along said curved end wall structure and increasing in depth from a minimum depth at said proximal end to a maximum depth greater than said minimum at said curved end wall sections; and said at plurality of aspiration openings being of elongate configuration and being located in said flexible and easily deformable wall and within respective aspiration relief channels and each being in communication with said aspiration chamber.

8. A cushioned aspirator appliance, comprising:

an elongate tubular element defining a flow passage and having a connection end and a distal end, said connection end being adapted for connection to a source of suction, said distal end defining an inlet opening to said flow passage; and a flexible cushioning tip of generally cylindrical configuration having a tubular portion being connected to and surrounding said distal end of said elongate tubular element and being composed of soft and resilient material of sufficient thickness and flexibility to present a cushioned portion for contact with the tissues of a patient and permitting flexing and yielding thereof by contact with patient body tissues, said flexible cushioning tip having a proximal end portion and a distal end portion, said tubular portion extending beyond said distal end of said elongate tubular element and defining a flexible and readily yieldable chamber wall section defining an aspiration chamber and having a curved distal end wall; and said flexible cushioning tip defining a plurality of external aspiration relief channels extending longitudinally thereof from said proximal end portion to said distal end portion and increasing gradually from a minimum depth at said proximal end to a maximum depth greater than said minimum depth at said curved distal end wall and defining a plurality of aspiration openings each being located in said flexible and readily yieldable chamber wall section and within one of said external aspiration relief channels and disposed in communication with said aspiration chamber and permitting flow of fluid therethrough into said aspiration chamber and into said flow passage of said elongate tubular element.

9. The formable cushioned tubular fluid handling appliance of claim 8, comprising:

a length of structural material being embedded within said elongate tubular element and extending substantially the entire length thereof, said length of structural material being manually formable to a desired configuration and causing said elongate tubular element to remain substantially as manually formed.

10. The formable cushioned tubular fluid handling appliance of claim 8, comprising:

said flexible cushioning tip defining an external periphery; and said plurality of external longitudinal aspiration relief channels being substantially evenly spaced about said external periphery of said flexible cushioning tip and extending from said abrupt proximal end to said rounded distal end, said external longitudinal aspiration relief channels having a minimum depth at said abrupt proximal end and having a maximum depth greater than said minimum depth at said rounded distal end.

11. The formable cushioned tubular fluid handling appliance of claim 8, comprising:

said tubular portion of said flexible cushioning tip and said elongate tubular element cooperatively defining at least one pressure relief passage relieving cement pressure during assembly of said flexible cushioning tip to said elongate tubular element and providing aspiration relief during aspiration.

12. An aspirator assembly for use during dental or medical procedures for removing body fluid and debris from the site of a procedure, comprising:

an elongate tubular element defining a flow passage and having a connection end and a distal end;

a flexible cushioning tip having a tubular connection section surrounding and establishing connection with said distal end of said elongate tubular element and being of sufficient thickness and resiliency to present a cushioned external surface for protective contact with the body tissues of a patient, said flexible cushioning tip having a proximal end and a distal end, said distal end defining a flexible tubular and readily yieldable chamber wall section extending beyond said distal end of said elongate tubular element and defining a rounded distal end wall portion and defining an aspiration chamber located beyond said distal end of said elongate tubular element; said flexible cushioning tip defining a plurality of external longitudinal aspiration relief channels extending along a major portion of said tubular tip head and terminating at said rounded distal end portion, said external longitudinal aspiration relief channels having gradually increasing depth from a minimum depth at said proximal end and a maximum depth greater than said minimum depth at said rounded distal end portion; and said flexible and readily yieldable chamber wall section of said flexible cushioning tip defining a plurality of aspiration openings each being located within one of said of said plurality of external longitudinal aspiration relief channels and permitting suction enhanced aspiration of fluid therethrough and into said aspiration chamber and thence into said flow passage of said elongate tubular element.

13. The aspirator assembly of claim 12, comprising:

internal longitudinally extending rib members being integral with said flexible and readily yieldable chamber wall section and projecting into said aspiration chamber of said flexible cushioning tip and defining a tube stop shoulder;

said elongate tubular element engaging said tube stop shoulder and limiting the position of said elongate tubular element within said tubular portion of said flexible cushioning tip; and said internal longitudinally extending rib members enhancing the structural integrity of said flexible and readily yieldable chamber wall section and restraining suction induced collapsing of said flexible cushioning tip and defining a fluid flow passage through said aspiration chamber in the event of collapse of said flexible cushioning tip by suction.

14. The aspirator assembly of claim 12, comprising:

an insert being located within said flexible cushioning tip and defining a stop shoulder positioned for contact by said distal end of said elongate tubular element, said insert defining a plurality of aspiration openings in communication with said plurality of external elongate aspiration relief channels and with said aspiration chamber.

15. The aspirator assembly of claim 12, comprising:

a length of structural material being embedded within said elongate tubular element and extending substantially the entire length thereof, said length of structural material being manually formable to a desired configuration and causing said elongate tubular element to remain substantially as manually formed.

16. The aspirator assembly of claim 12, comprising:

a plurality of internal longitudinally extending rib members being integral with said flexible and readily yieldable chamber wall section and projecting into said aspiration chamber and being positioned for tip body supporting contact with one another upon suction induced collapse of said flexible and readily yieldable chamber wall section of said flexible cushioning tip and defining fluid flow channels from said aspiration openings through said aspiration chamber and to said flow passage of said elongate tubular element.

* * * * *